United States Patent
Artusy et al.

(10) Patent No.: US 11,069,437 B1
(45) Date of Patent: Jul. 20, 2021

(54) DISTRIBUTED COMPUTER SYSTEM FOR COORDINATING MESSAGING AND FUNDING FOR HEALTHCARE EXPENSES INCLUDING FUNDING VIA NETWORKED CROWDSOURCING

(71) Applicant: Exurgo, Inc., Saratoga, CA (US)

(72) Inventors: Ladan Aslani Artusy, Saratoga, CA (US); Donna Victoria Artusy, Saratoga, CA (US)

(73) Assignee: EXURGO, INC., Saratoga, CA (US)

( * ) Notice: Subject to any disclaimer, the term of this patent is extended or adjusted under 35 U.S.C. 154(b) by 277 days.

(21) Appl. No.: 16/166,002

(22) Filed: Oct. 19, 2018

Related U.S. Application Data

(63) Continuation-in-part of application No. 15/233,786, filed on Aug. 10, 2016, now abandoned.

(60) Provisional application No. 62/205,499, filed on Aug. 14, 2015.

(51) Int. Cl.
 *G06Q 30/00* (2012.01)
 *G16H 20/40* (2018.01)
 *G16H 80/00* (2018.01)
 *G16H 10/60* (2018.01)
 *G06Q 30/02* (2012.01)

(52) U.S. Cl.
 CPC ......... *G16H 20/40* (2018.01); *G06Q 30/0279* (2013.01); *G16H 10/60* (2018.01); *G16H 80/00* (2018.01)

(58) Field of Classification Search
 None
 See application file for complete search history.

(56) References Cited

U.S. PATENT DOCUMENTS

| | | | |
|---|---|---|---|
| 8,209,194 B1* | 6/2012 | Nidy | G06Q 40/04 |
| | | | 705/2 |
| 9,058,591 B2 | 6/2015 | Killoran, Jr. et al. | |
| 2003/0229507 A1* | 12/2003 | Perge | G06Q 30/0279 |
| | | | 705/36 R |
| 2011/0264460 A1 | 10/2011 | Jagemann et al. | |
| 2012/0123789 A1 | 5/2012 | Patel | |
| 2013/0030828 A1* | 1/2013 | Pourfallah | G06Q 20/384 |
| | | | 705/2 |
| 2013/0304486 A1 | 11/2013 | Jagemann et al. | |
| 2016/0012197 A1 | 1/2016 | Eromo et al. | |

OTHER PUBLICATIONS

Frequently Asked Questions, Watsi, copyright 2016 [retrieved Dec. 30, 2016], https://watsi.org/faq, 8 pages.

(Continued)

*Primary Examiner* — Narayanswamy Subramanian
(74) *Attorney, Agent, or Firm* — Jacob M. Ward; Ward Law Office LLC

(57) ABSTRACT

A distributed computer system comprises one or more patient system, configured to be operated by patients seeking provider services, a front-end web server to interface to the one or more patient system, a back-end server system coupled to the front-end web server to receive patient information, a healthcare provider system that provides information about a procedure needed by a patient unable to pay for the procedure, providing the information to the back-end server system, and a donor computer system, for accepting and receiving messages from the back-end server system about funding patient procedures.

8 Claims, 12 Drawing Sheets

(56) References Cited

OTHER PUBLICATIONS

Janah, "Why We Merged: Samahope and the Case for Nonprofit M&A," Medium, Apr. 6, 2016 [retrieved Nov. 16, 2016], https://medium.com/@leilajanah/why-we-merged-samahope-and-the-case-for-nonprofit-m-a-d3a68de03d4d#.s760zouuh, 3 pages.

Peterson-Withorn, "Samahope's Leila Janah: $3 Can Save the World," Forbes, Oct. 21, 2014 [retrieved Nov. 16, 2016], http://onforb.es/1pczjgJ, 2 pages.

* cited by examiner

DISTRIBUTED COMPUTER SYSTEM FOR COORDINATING MESSAGING AND FUNDING FOR HEALTHCARE EXPENSES INCLUDING FUNDING VIA NETWORKED CROWDSOURCING

FIELD OF THE INVENTION

This application is a continuation-in-part of U.S. patent application Ser. No. 15/233,786 filed Aug. 10, 2016, which in turn claims the benefit of, and is a non-provisional of, U.S. Provisional Patent Application No. 62/205,499 filed Aug. 14, 2015 entitled "Networked Crowdsourcing of Healthcare Expenses". The entire disclosure of applications recited above is hereby incorporated by reference, as if set forth in full in this document, for all purposes.

BACKGROUND OF THE INVENTION

Healthcare costs can limit the availability of hospital procedures for some patients in need of those procedures. Patients who are without healthcare coverage, who are in the low to medium income brackets and have not registered through market exchanges or who cannot afford such premiums even with government subsidies, have trouble obtaining healthcare services, or have insurance but it is insufficient. Additionally, there are patients who have insurance or can pay, but paying medical expenses could result in financial hardship and/or bankruptcy. Some patients might be able to access alternative sources of funding for healthcare expenses, but this can be a complicated process to coordinate, as donors and providers and patients might only have access to disparate computing systems.

SUMMARY OF THE INVENTION

A method of coordinating healthcare accessibility and funding for healthcare procedures, comprising: obtaining, request from patients and from a healthcare provider, information about a procedure needed by/for a patient unable to pay for the procedure; obtaining, from donors, funds to cover such procedures; and providing funding from those donors to the healthcare provider.

The following detailed description together with the accompanying drawings will provide a better understanding of the nature and advantages of the present invention.

DETAILED DESCRIPTION OF THE INVENTION

Figure 1:
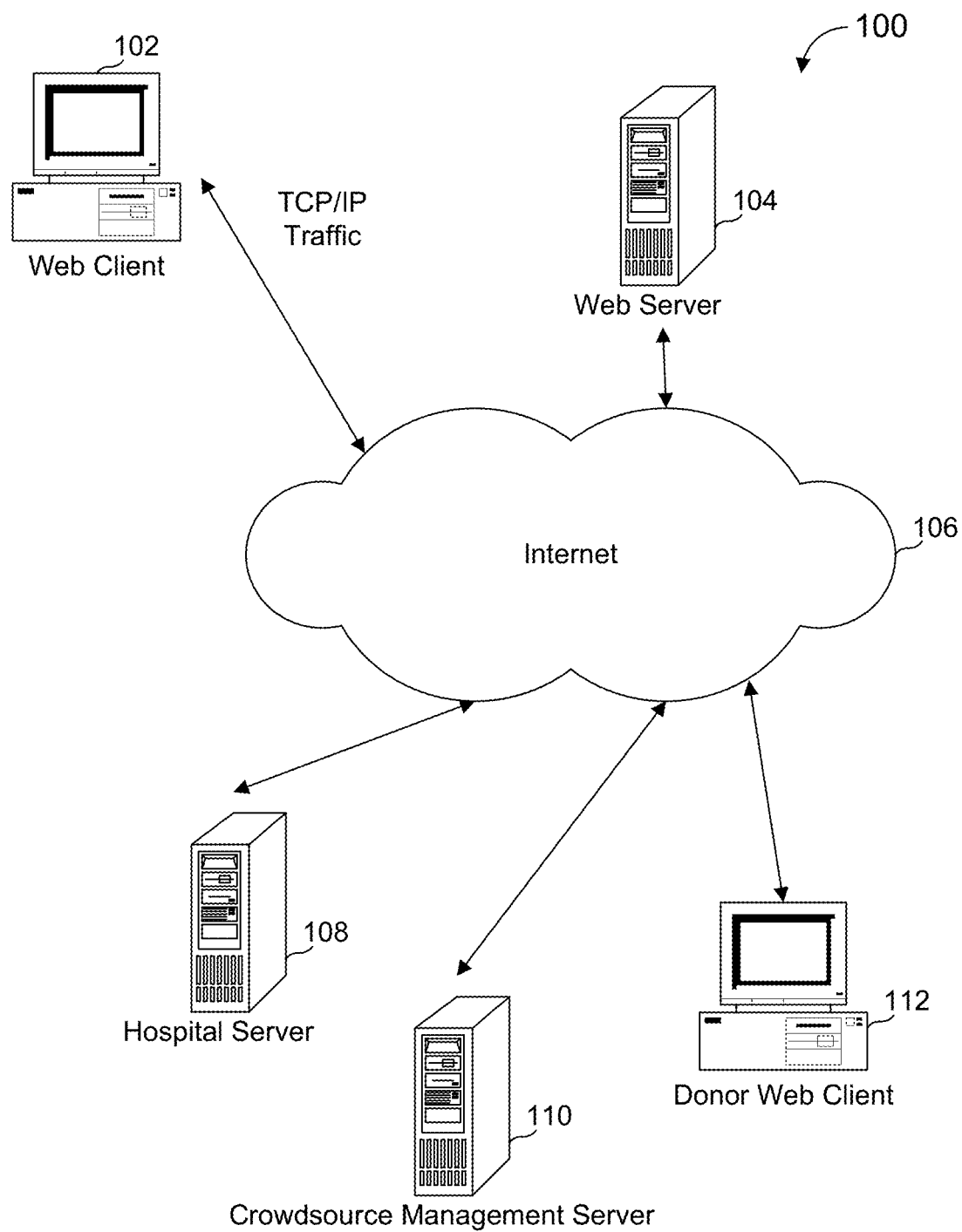
FIG. 1 illustrates an example of a computer system that might connect various parties in a healthcare crowdfunding system.

Using the methods and apparatus described herein, patients without health coverage can obtain medical care identifying and collecting curated patients' information, distributing the collected data to one or a few pre-selected healthcare provider(s) that are cross-referenced to screen for the ability and willingness to provide treatment of patient condition(s), and selecting and matching from diverse financial donors (such as private, public and governmental) for a funding process that is facilitated by the computer system described herein. This method presents a great opportunity to serve the marginalized sector of the population, to reduce the financial drain of hospitals (especially, but not limited to, those that are community based and not-for-profit), and to lessen the burden on the government and its assistance programs. It also will reduce medical costs and economic opportunity loss in the long run.

A sudden illness, an accident, or long-term care needs, can cause an insurmountable financial burden especially for those who already struggle to make ends meet. On the other hand, healthcare providers, namely hospitals, are faced with rising expenses and uncompensated care costs. Despite costly collection processes, bad debt, which is primarily comprised of unpaid medical expenses caused by patients who cannot afford to pay their obligation, is not reimbursable. Hospitals would like to reduce their costs for uncompensated care to their patients. There are mandates that require all non-profit hospitals to provide community-based services in order to maintain their tax-exempt (federal and local) status.

With an increasing number of patients foregoing necessary medical care because of the cost, solutions are needed. Using such a networked matching system embodying a plurality of computers to collect, retrieve and match patients, medical care providers (such as hospitals) and financial donors to efficiently, accurately, cost-effectively, and expeditiously enroll in a crowdsourcing/crowdfunding service. The patient could either directly or through a healthcare provider request for a service. The information that is screened by the hospital with assurances of privacy and is sent with a request to a funding management system computer, which then posts and presents the request to a variety of donors, such as foundations, companies and individuals. Examples are described below. Those donors can offer to cover specific requests or a blanket set of requests, and the funding computer informs the hospital computer accordingly so that the procedure can be performed. Of course, emergency care that cannot be quickly funded might not go through this process.

An integrated technology system and crowdfunding platform can partner with healthcare organizations to facilitate the flow of capital in exchange for value-based and uninterrupted healthcare delivery to patients. This crowdfunding platform can be used by patients who are in pre-scheduled surgery associated with acute or chronic conditions, and those in long-term care. The collected proceeds from campaigns can be used to compensate the healthcare providers that offer healthcare delivery with full transparency to the stakeholders while maintaining the privacy of the patient.

Depending upon the urgency of the care, some campaigns will be run on an Emergency Alert System (EAS) system. Smartphone apps and computer programs might be used as the interface for such campaigns. This might facilitate intergenerational assistance, such as by those who would like to help their elderly parents or loved ones, as well as the indigent population itself. Some programs as part of the platform might be in the form of automated interaction agents (e.g., "chatbots") that provide assistance with getting information and providing tutorials and other resources to provide guidance and support to patients and designated caretakers.

Using a distributed computing system, involving patient computers used by patients, a front-end interface, such as a web server, for interactions with patients, and a back-end server that coordinates traffic and interactions between the patients (via the front-end interface), provider computer systems used to manage provider practices (patient electronic records, billing, etc.) and donor computer systems used to manage and specify donor terms of donations. Most aspects are automated, so that once a patient inputs relevant data, the back-end server can coordinate with other computer systems to arrange for funding a procedure and scheduling that procedure.

The back-end server also manages filtering, such as filtering for patients to filter for those who would benefit from a specified procedure and would not be able to obtain that procedure without alternative funding, for providers to those who are able and willing to provide the treatment of patient condition, and for donors who agree to fund those patients for those treatments. The back-end server might also manage harmonizing, standardizing, and curating. In this manner, the distributed computing system can identify and collect curated patients' information, distribute the collected data to one or more pre-selected healthcare providers, and select and match a financial donor. Donors might be from diverse backgrounds (private, public and governmental). This process involves multidimensional analysis and classification of data that is trackable with full transparency. It embodies networked matching systems that includes a plurality of computers to collect, retrieve and match patients, medical care providers (hospitals) and financial donors to efficiently, accurately, cost-effectively, and expeditiously provide value-based care to underserved patients who have limited financial means.

The platform might also include a telemedicine module. The healthcare providers can use this telemedicine module to provide information and advice to patients, as well as acting as an initial onramp into the platform to inform hospitals and donors about patients' healthcare needs. Medical satellite offices or safety net clinics either in rural or urban areas that are equipped with such technology can send an alert message to a funding management system if the patient's profile matches predetermined requirements. Thus, when the patient is diagnosed and ready for treatment, there will be enough time to secure funding for the medical procedure so the patient receives the timeliest care.

Campaigns and donations could be managed and tracked in a database.

An optional time-banking feature might be implemented in some variations, wherein a virtual or alternative currency is maintained by the system based on the reciprocity of labor hours, which can strengthen community involvement (without tax implications), and encourage self-reliance and dignity, as there is reciprocity of services without being perceived as charitable handouts. Time banking, also known time-based currency or time dollars, can be a tax-exempt alternative and complementary currency whose unit is based on time. For example, one hour of time contributed might be equivalent to one time dollar or time credit, regardless of service. This alternative currency can be integrated into the platform for patients with mental health condition and long-term care. Studies have shown that using time banking alleviates monetary burden in a traditional sense, but also increases community participation and reciprocity of help as well as increases self-esteem. It dignifies the process by moving away from handouts and charity model towards the power of earning and self-reliance.

The integrated technology and crowdsourcing crowdfunding platform can be configured to process different categories of patients differently. For example the platform might use different processes for acute patients, chronic patients and long-term care patients. Healthcare provisions might include pre-surgery candidates (for example, for cardiovascular surgery), addressing patients who need ongoing monitoring and treatments (for example, chemotherapy patients), and long-term medical care (for example, Alzheimer's patients).

The platform can comprise a plurality of distributed computer systems involving one or more patient systems, a front-end web server to interface to the one or more patient systems, a back-end server system coupled to the front-end web server to receive patient information, a healthcare provider system and a donor computer system. The healthcare provider system might provide information about a procedure needed by a patient unable to pay for the procedure, providing the information to the back-end server system. The donor computer system might accept and receive messages from the back-end server system about funding patient procedures. The one or more patient systems might be configured to be operated by patients seeking provider services. The distributed computer system might also include a matching module that processes a plurality of patient requests and a plurality of donor records to derive a matched set of donor requests wherein the matched set of donor requests optimizes a number of procedures that can be funded.

Using this platform for managing funding of healthcare procedures might involve receiving a request for medical care directly from a patient, obtaining, from a healthcare provider computer system operated for a healthcare provider, information about a procedure needed by a patient unable to pay for the procedure, obtaining, from donor computer systems remote from the healthcare provider computer system, messages corresponding to funds to cover such procedures, wherein the donor computer system maintains donor records indicating types of procedures a donor supports and will fund, filtering and/or curating the request for medical care based on facility records indicating that the procedure is fundable, and providing funding from those donors to the healthcare provider.

In some embodiments, the process also includes receiving, at a healthcare facility computer system, a request for medical care, wherein the request for medical care is a first request initiated by a patient and recorded in the healthcare facility computer system, obtaining, in the healthcare facility computer system, a procedure record that includes data about a procedure that corresponds to the first request for medical care, determining, using the healthcare facility computer system, that the patient requires the procedure and that the patient is unable to pay costs of the procedure, accessing a donor database to identify, in the donor database, donor records corresponding to donors that have identified donation criteria and that are donor records with identified donation criteria that match the procedure referenced in the procedure record, and filtering and/or curating a plurality of requests including the first request to a filtered set of filtered requests wherein each filtered request relates a related procedure record and a related donor record. For each of the filtered and/or standardized and/or curated requests, a donor request message might be sent with patient details and procedure details to a donor computer system of a selected donor, wherein the donor request message indicates a consistency between a filtered and/or standardized and/or curated request and donor donation criteria, followed by receiving approval from the donor computer system for the selected donor to fund the procedure, and effecting funds transfer from the selected donor to a healthcare facility operator for the procedure.

The donor request message with the patient details might include sufficient information for the selected donor to determine that funding is appropriate and omits patient personally identifying information. The donor records corresponding to the donors that have identified donation criteria might indicate domains of interest for each donor.

The process might also include matching a plurality of patient requests and a plurality of donors, using a healthcare facility computer system, that processes a plurality of patient requests and a plurality of donor records to derive a matched set of donor requests wherein the matched set of donor requests optimizes a number of procedures that can be funded.

Example System

This section describes an example of using the system described herein for prescheduled surgery and a long-term method.

FIG. 1 illustrates an example of a computer system that might connect various parties in a healthcare crowdsourcing crowdfunding system.

Consider a patient, P, with a history of cardiovascular diseases who is a candidate for a pacemaker implant but is unable to pay for the procedure. Suppose P visits a hospital to schedule a surgery. An administrator at the hospital will take the patient's medical and financial information. The patient will be scheduled to have a consultation with a cardiologist and a surgeon (often not the same) for an evaluation and surgery, respectively. The medical information will travel through the healthcare provider's computer system as is done with other patients who are able to pay either out of pocket or through insurance. The administrator would note in the patient record a categorization, perhaps by selecting a specific code, that the patient is to move within the crowdsourcing method system described herein. The categorization would relieve patient P from full or partial financial responsibility associated with the medical service, depending on their financial capacity. The specific code might be shielded and remain confidential from the medical service provider to ensure that the quality of care is unaffected. The estimated associated expenses report for doctors' services, surgery cost and cost of hospital stay for recovery will be sent to the crowdfunding platform, such as the funding management system 206. The funding management system 206 might signal to the other participating computers what to use as the specific code.

Figure 2:
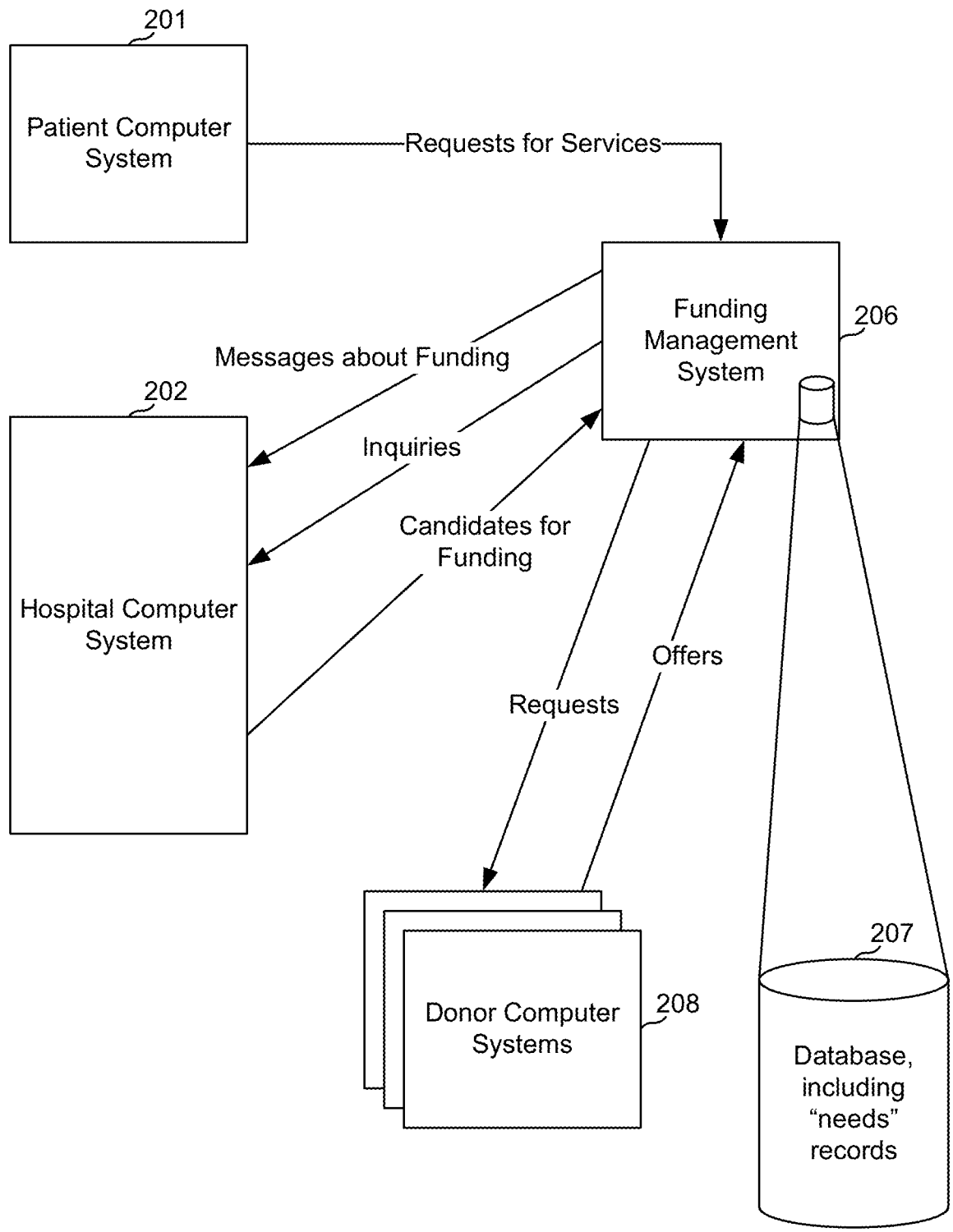
FIG. 2 illustrates message flows between the various systems.

FIG. 2 illustrates message flows between the various systems.

An administrator of the crowdfunding platform can review the patient's information that the hospital computer provided. Not all patient or healthcare provider information needs to be provided; the privacy level of the patient would be determined at the hospital by the patient. The hospital determines what information will be necessary to be revealed for the collection of the funds, while maintaining and protecting the patient's privacy. The patient might be asked (patient computer system 201) whether to be presented anonymously or publicly for financial assistance. Additional information will be helpful when using social media to promote certain campaigns, but is not necessary to receive funding. The crowdfunding platform computer then requests an explicit written consent from the patient, once at the beginning when patient's intake is taken, and later when the patient is ready to receive the medical treatment, thereby ensuring patients' rights are protected.

Once the information is received by the funding management system (206) and reviewed, a copy will be stored in the database and a copy will be forwarded to the donor computer system (208). Donor Computer Systems (208) includes private foundations, corporate foundations, corporate giving programs, and the general public outreach via social media. Two example scenarios to obtain the funds for the healthcare services are funding from an all donors' category (private foundations, corporate foundations, and corporate giving programs) and funding addressing the general public. One method is that a fund pool is created in advance from the institutional donor category and be assigned with any specifics and criteria requested from the donor. Though these funds will be earmarked and promised by the donor(s), they will not be available to the funding management system (206) for distribution until a bill from the hospital is generated with all the details. This way, the donor will feel reassured that their funding will be properly allocated and remain in a secure account until funds are needed. The second method is addressing institutional donors and the general public, in which case no pool of funds is created, and donors would opt to review and provide funds as need arises on a case-by-case basis.

In one scenario, if a certain amount of funds has been negotiated and dedicated in advance for such cases, the donor will send a consent notification to the funding management system (206), noting that the funds will become available upon completion of the service. Once the patient goes through the operation and the recovery, the hospital issues the bill and notifies the funding management system (206) with all the breakdowns of the bill(s). The funding management system (206) forwards the entire bill to the funding entity donor computer systems (208). The full amount of bill(s) will be forwarded to funding management system (206). The funding management system (206) will reimburse the healthcare provider for either a partial amount or the full amount, minus x % pre-negotiated (with the hospital/service providers) fee for service. This fee covers the general, administrative and operational expenses for the platform manager. The fund for medical services gets transferred from the database to the hospital billing services (202).

In a second scenario, if a certain amount of funding has not been negotiated and dedicated in advance from the funding partners (as some foundations might prefer not to set aside the fund), the patient's campaign will be sent widespread to all donors including the general public via social media. Once the necessary amount of funds has been collected to cover the medical expenses, the process duplicates itself as in case of the first scenario.

Patients can include adults (including seniors) and children up to 18 years old who require long-term and ongoing medical care to improve the quality of life and extend the length of life by such care. Some examples of such conditions that will require long-term care are: Alzheimer's disease, neurodegenerative and cardiovascular diseases, cancer, diabetes, auto immune disorders, kidney failure, mental illnesses including post-traumatic stress disorder (PTSD), geriatric and elder care, etc. In such scenarios, steps for funding may remain the same as for the pre-scheduled surgery patients except that the costs are recurring. For these situations, the request for funds may cover some period of time, such as six consecutive months of treatment. In a specific implementation, one month prior to the due date (fifth month), the funding management system will request an evaluation from the healthcare provider. The result will be forwarded to the donors and the process will duplicate itself for the collection of funds for another six months.

Using this system, the funding coordinator partners with healthcare providers themselves as the first point of contact to be able to understand the institutions' obligations and patients' needs before and after the treatment. Then, the funding coordinator might approach corporations, foundations, philanthropic communities and the general public to maximize outreach with a strong positive impact to fulfill a mission of serving the underserved, and to encourage value-based healthcare deliveries that are presented/carried out with full transparency.

Funding might also be arranged from private or government contributors for veteran healthcare services, such as those dealing with trauma, mental or physical ailments such as spinal cord impairment, traumatic brain injury, Post-Traumatic Stress Disorder (PTSD), schizophrenia, depression, military sexual assault trauma, substance abuse, and concussion.

Figure 3:
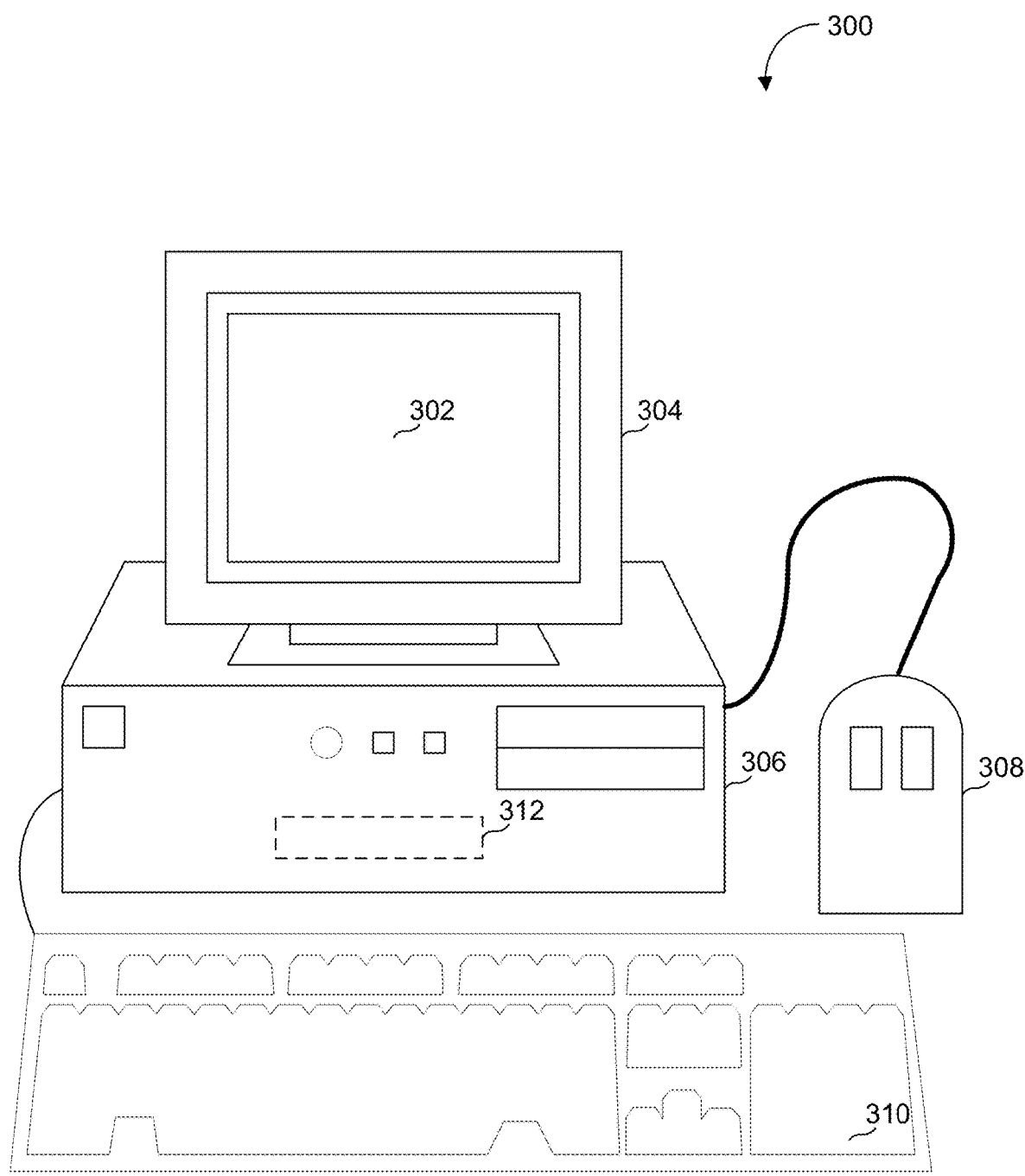
FIG. 3 illustrates a computer that might be used as a client or server.

FIG. 3 illustrates a computer that might be used as a client or server.

Figure 4:
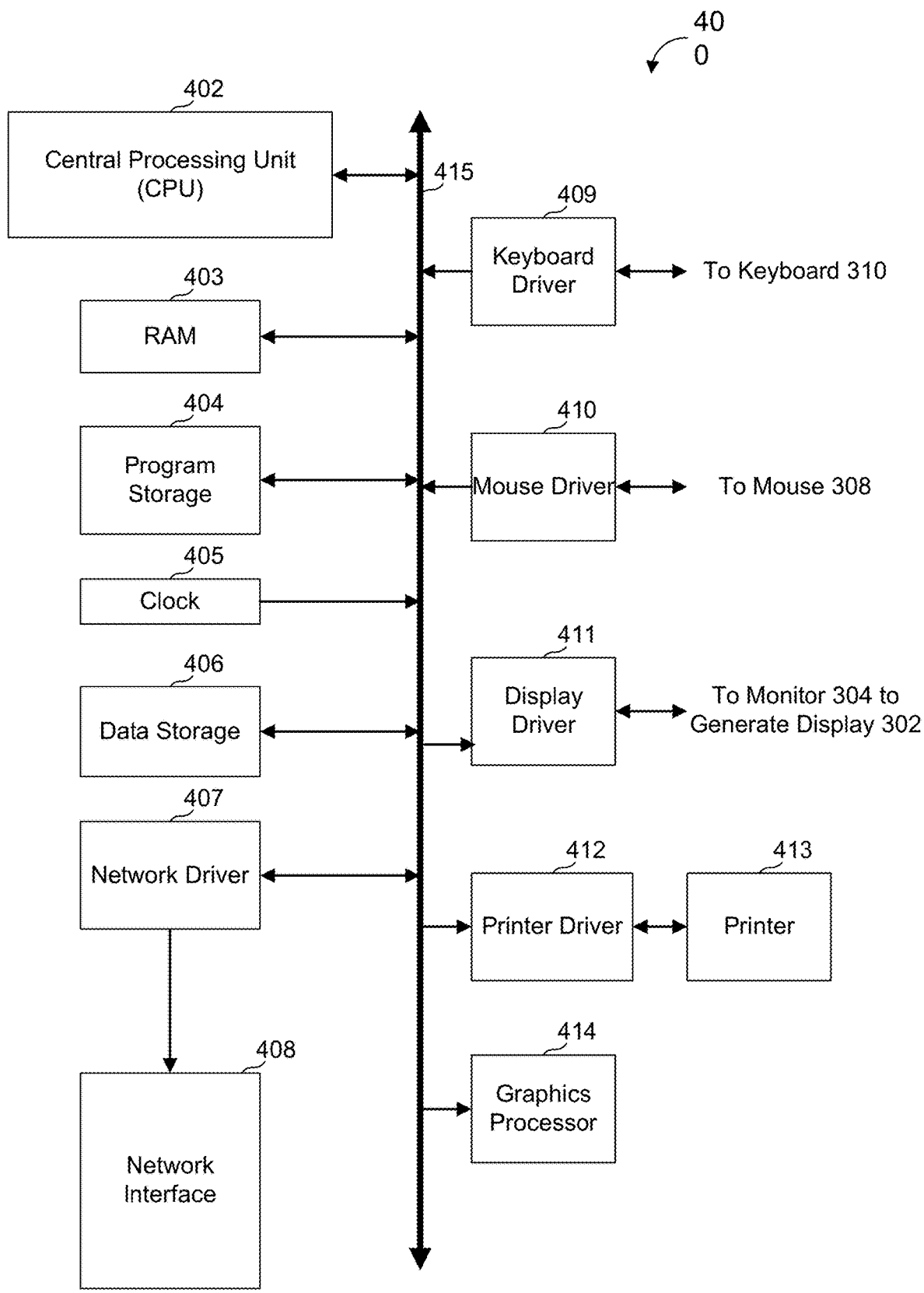
FIG. 4 illustrates the computer in more detail.

FIG. 4 illustrates the computer in more detail.

Figure 5:
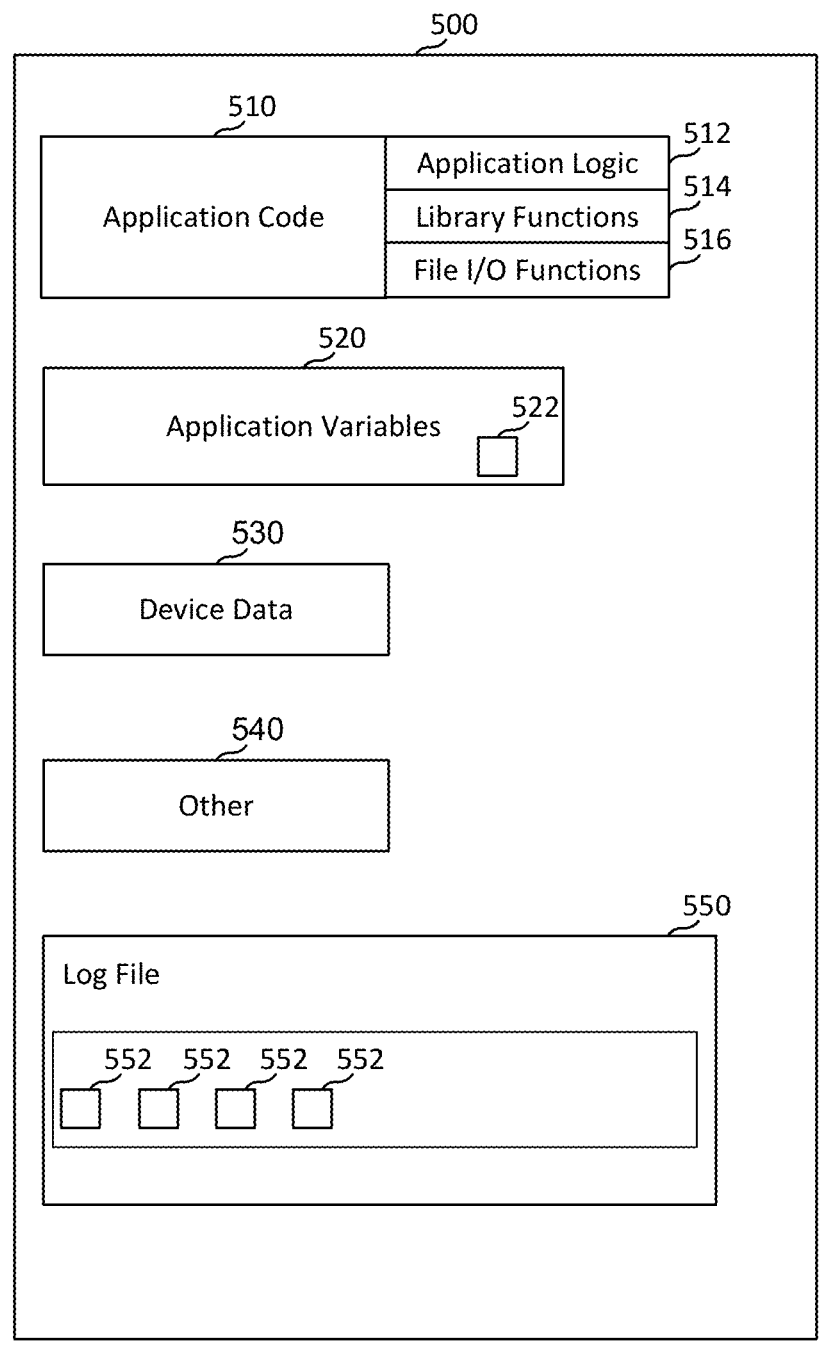
FIG. 5 illustrates components of memory that might be present in the computer.

FIG. 5 illustrates components of memory that might be present in the computer.

Figure 6:
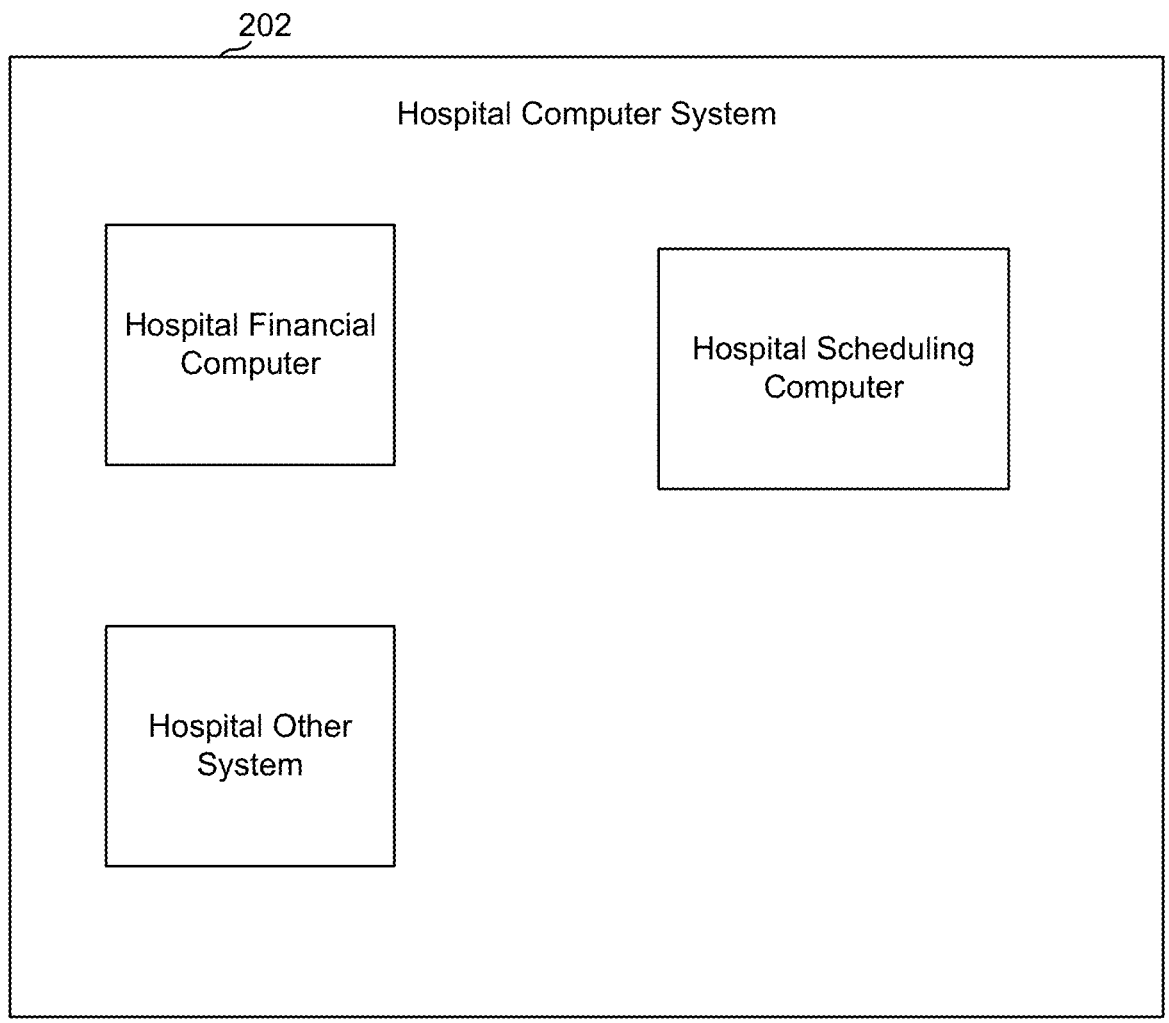
FIG. 6 illustrates the healthcare server in more detail.

FIG. 6 illustrates the healthcare server in more detail.

Figure 7:
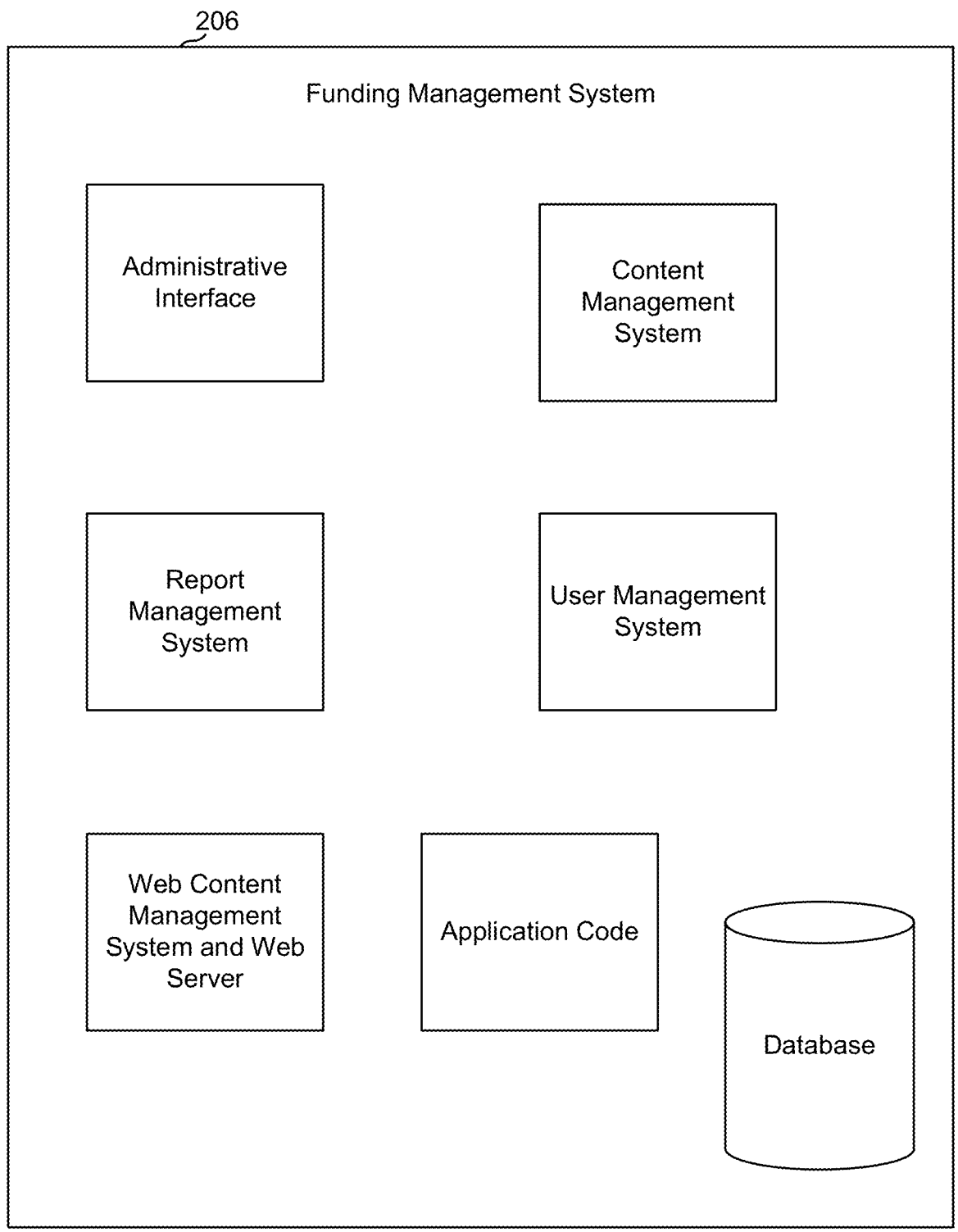
FIG. 7 illustrates the funding server in more detail.

FIG. 7 illustrates the funding server in more detail.

Figure 8:
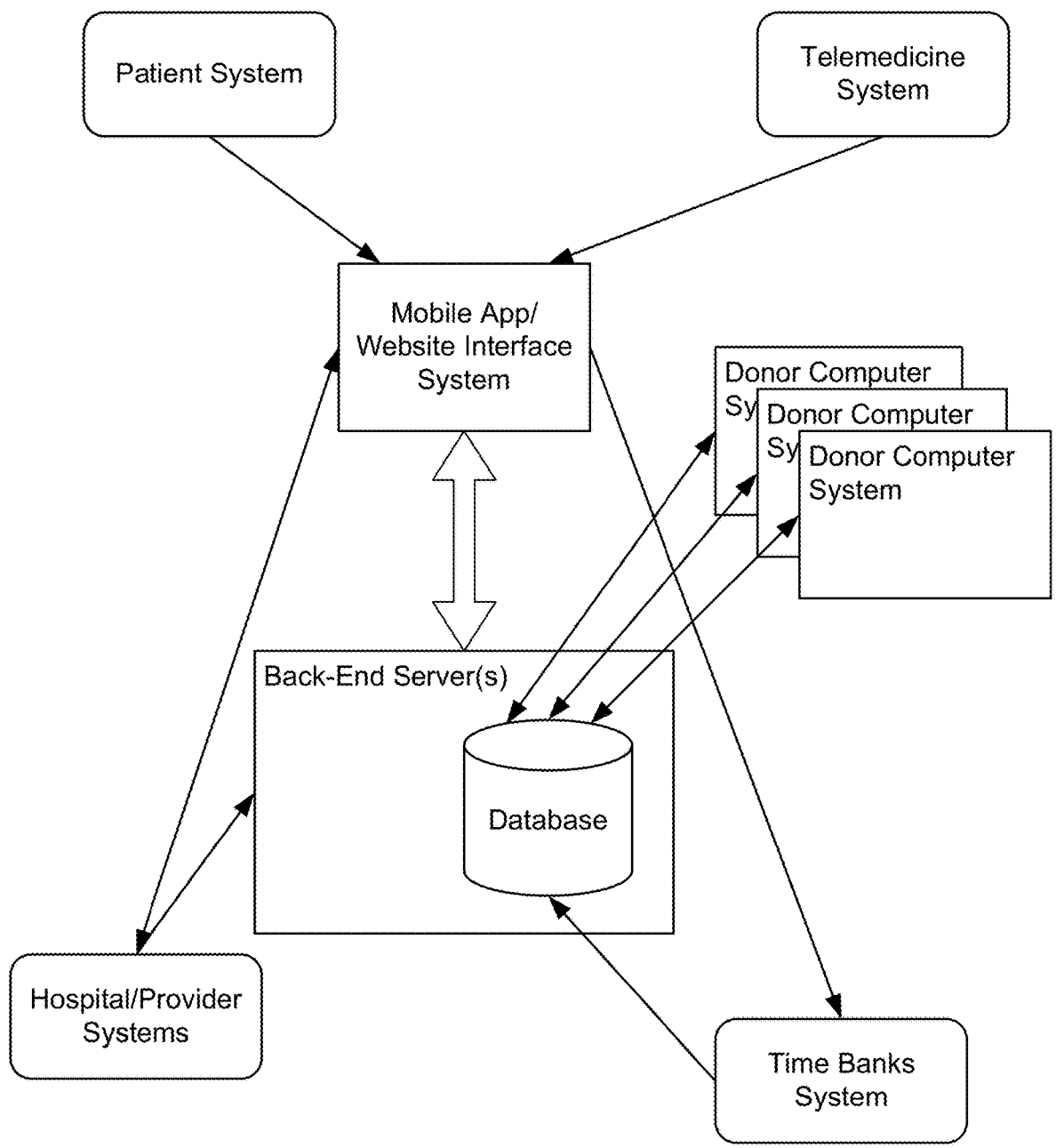
FIG. 8 illustrates message flows in an alternative embodiment.

FIG. 8 illustrates message flows in an alternative embodiment.

Figure 9:
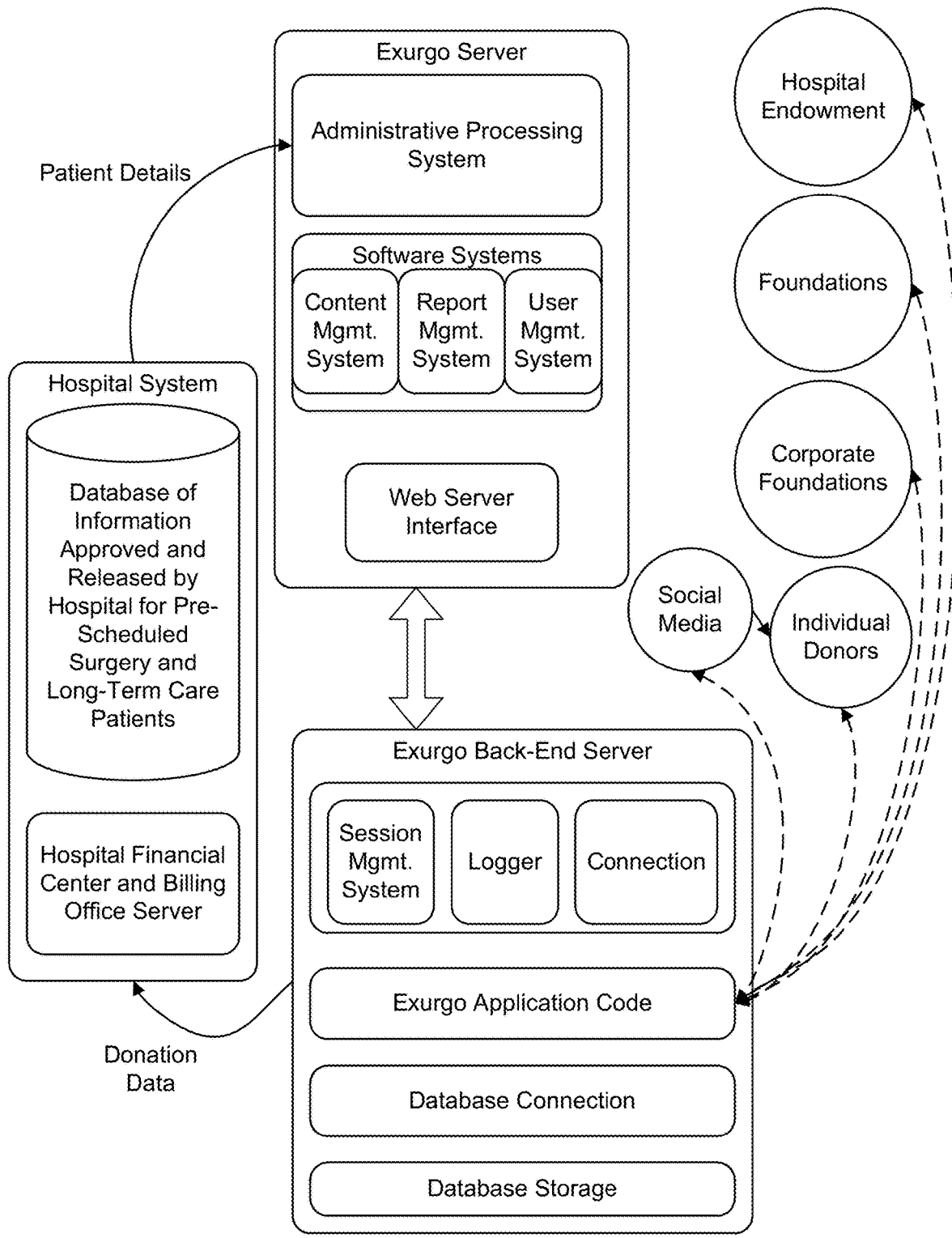
FIG. 9 illustrates message flows between the various systems in an alternative embodiment.

FIG. 9 illustrates message flows between the various systems in an alternative embodiment.

Example Distributed Server System

Figure 10:
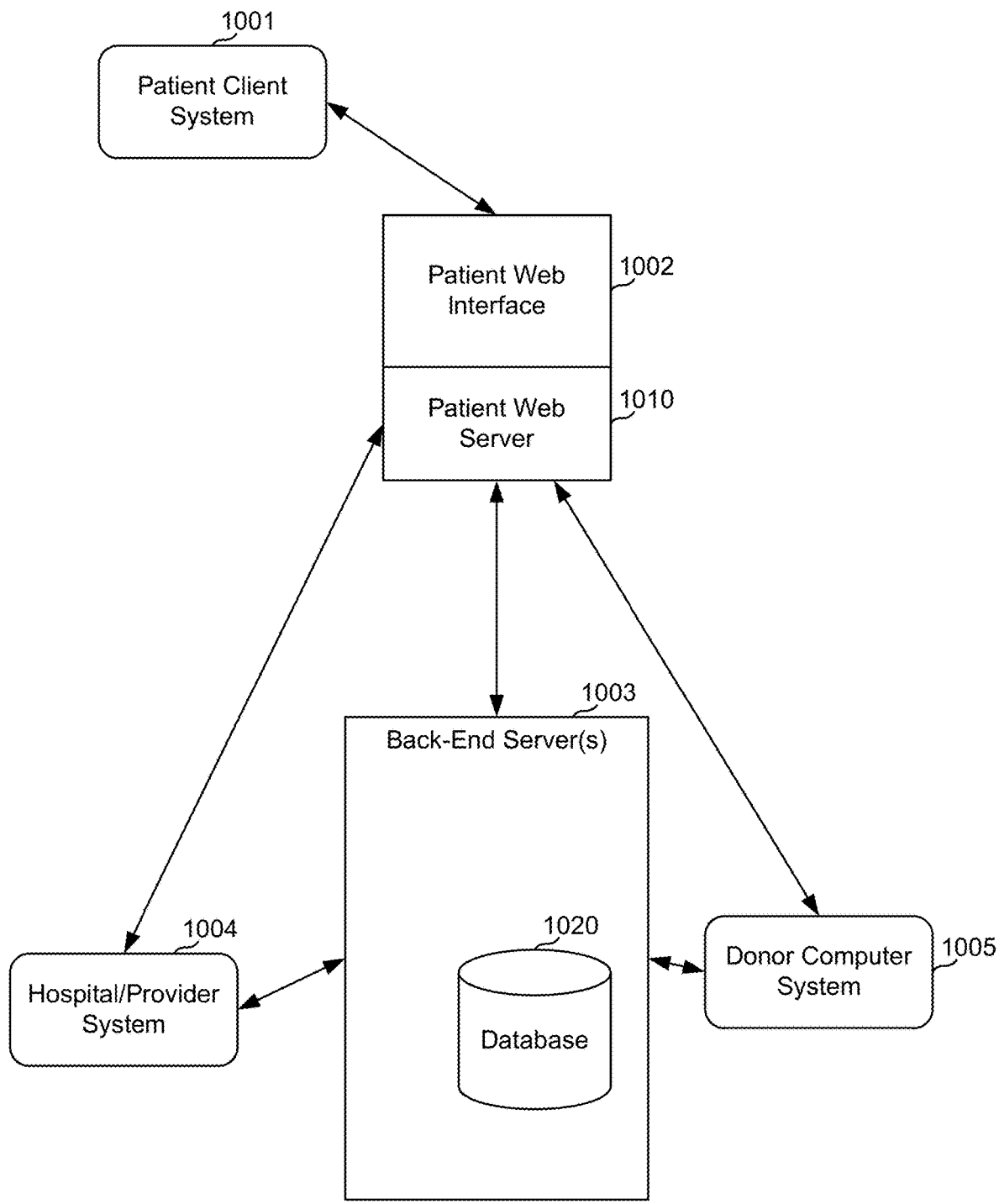
FIG. 10 illustrates various system components.

Another example implementation uses the distributed server system illustrated in FIG. 10. As shown there, five major components might be contemplated: a patient client computer (system or device) 1001, a patient webserver 1010 and web interface 1002, a back-end server 1003, one or more provider servers 1004, and one or more donor servers 1005. While details might be described below with reference to a single provider server or a single donor server, a typical system would have multiple patient client computers, multiple provider servers, and multiple donor servers.

Figure 11:
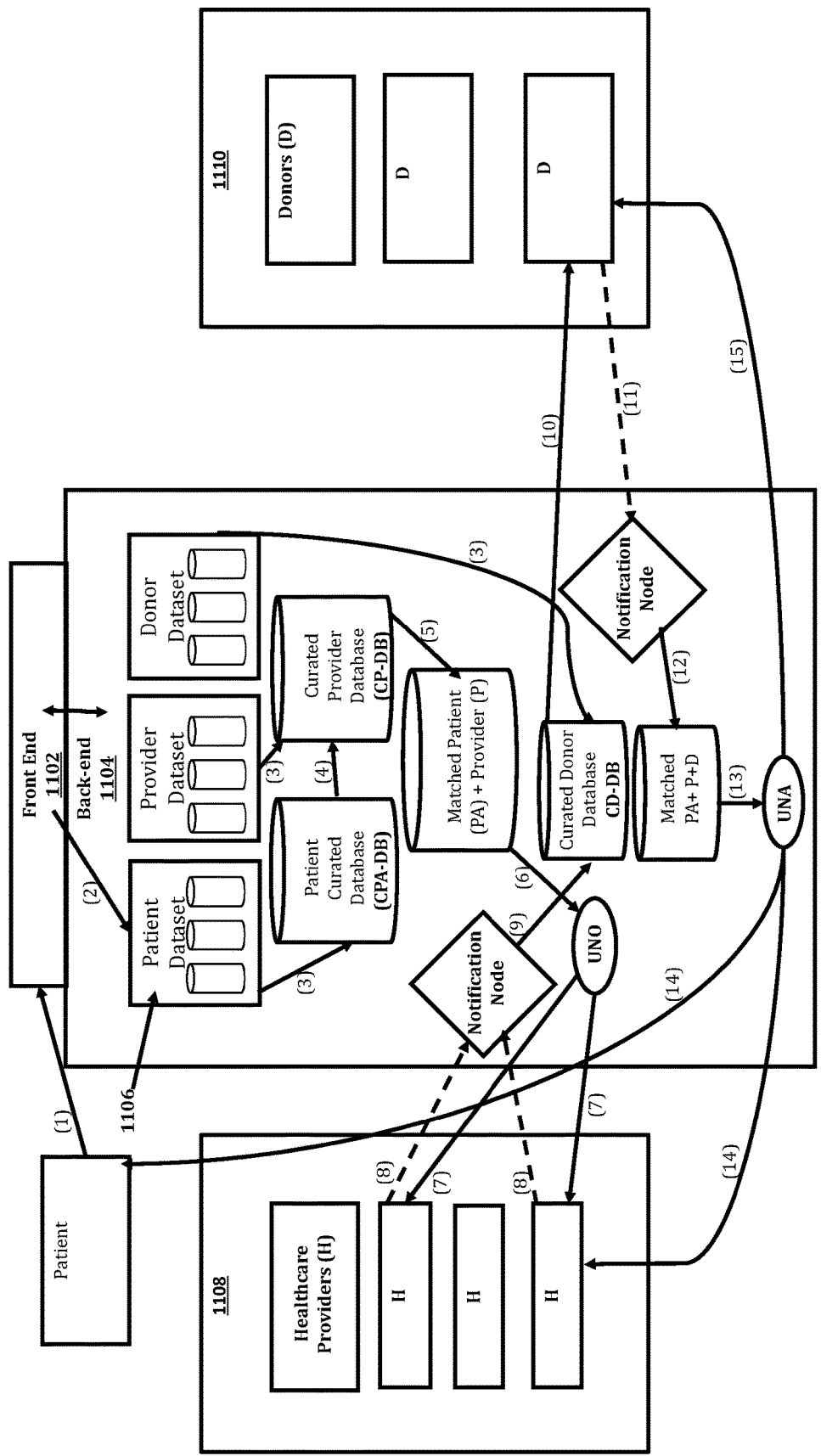
FIG. 11 illustrates various system components and process flows between components.

The patient webserver 1010 includes program code for creating browser pages to get information from a patient such that a patient might enter information using the patient client computer 1001. The patient client computer 1001 might be a patient's smartphone, laptop, or a kiosk provided by a health care facility. The patient interface 1002 provides the user interface for obtaining patient information as described herein. In one particular process, the patient uses patient client computer 1001 to input patient information and that patient information is recorded by patient webserver 1010 and/or transmitted to back-end server 1003, which then records that patient information into a patient database 1020. Using this, a patient can connect to a front-end system to input required information for a medical treatment and payment request. In FIG. 11, this is illustrated by process flow 1 (symbolized with an arrow labeled with a circle around "1").

In process flow 2, a front-end server 1102 transmits the patient's information to a backend server 1104 and the backend server 1104 stores that into a patient repository dataset (PA-Dataset1) 1106. A business/application logic module of the backend server 1104 harmonizes and standardizes patient data and generates a unique identifier code (UIC) for the patient. In process flow 3, the business/application logic module stores the UIC with patient data into a curated patient database (CPA-DB).

The business/application logic module also normalizes and standardizes data about provider(s) and donor(s), from a provider silo 1108 and a donor silo 1110, respectively. The business/application logic module stores the normalized and standardized data into a curated provider database (CP-DB) and a curated donor database (CD-DB), in process flows 3 and 4.

In order to match a medical request with a provider, the logic module might prompt a corresponding request that might be a CRUD operation (create, read, update, delete) from curated provider database and the curated patient's dataset. In process flow 5, the logic module stores matched patient/provider data in a patient/provider database (PA+P), marked with unique patient/provider codes.

In process flow 6, the logic module generates a real-time message in the form of an Urgent Notification (UNo) message. The back-end server transmits, in process flow 7, the UNo message to a listing of pre-selected medical provider(s), alerting them of a need/match, and requesting a real-time response of accepting or declining the patient. One or more provider systems might reply, in process flow 8, to a notification node of back-end server 1104.

Upon the receipt of approval for treatment from a provider system, the notification node sends, in process flow 9, matched patient and provider data to a curated donor database (CD-DB). A donor query module, in process flow 10, sends a message to a donor system, or relies on an existing pool of funds established and available from authenticated donor(s) for such treatment. In process flow 11, the donor system sends a notification to a second notification node of the back-end server. In process flow 12, upon receipt of approval for pledge of medical payment from a donor, the back-end server stores matched patient, provider, donor data in a matched curated PA, P, D database with special coding to proceed for further actions.

In process flows 13, 14 and 15, when the back-end server notes an update in the PA+P+D database, it generates and sends a real-time Urgent Notification Approval (UNA) message to the stakeholders (e.g., the patient, the provider, the donor). The patient system and provider systems receive the message. The donor system receives a notification that the process is commencing (process flow 15).

Figure 12:
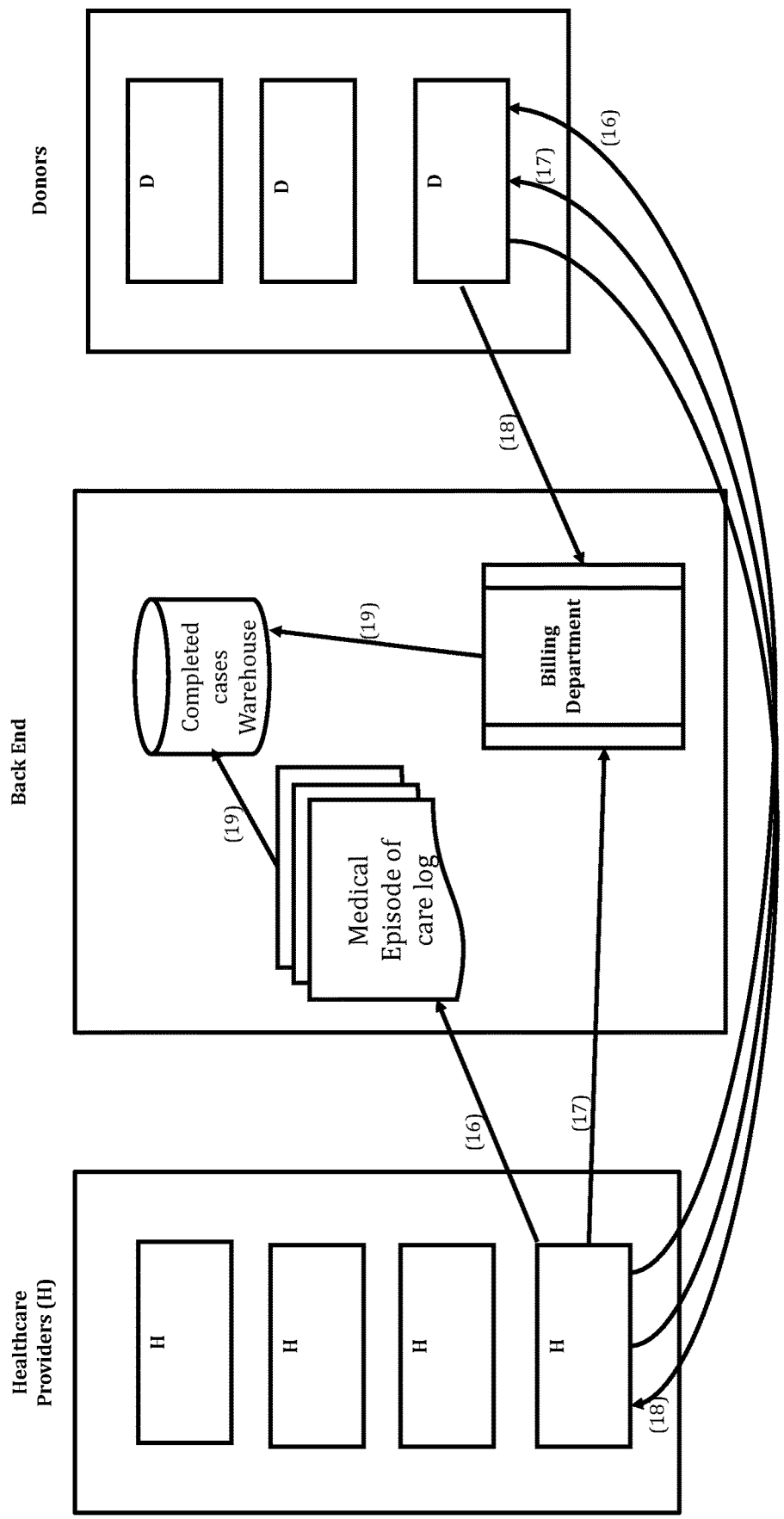
FIG. 12 illustrates various system components and process flows between components.

FIG. 12 illustrates additional process flows.

During the process of the treatment, the back-end server system documents each stage of the health episode and the associated costs. The provider sends the episode of care log to the back-end server and the donor system in process flows 16 and 17. This process induces, cost saving, efficiency and transparency.

The provider system also sends a final report summing the total bill for the treatment to the donor and to the back-end system. Upon completion of the donor's review, in process flow 18, the donor system signals to the back-end server that the designated funds should be distributed.

In process flow 19, the back-end server files financial reports from a billing database and from episode of care files into a completed cases warehouse.

Curation

One aspect of an implementation that drives efficiency of the distributed computer system is being able to curate and filter patients, providers and donors, as a matching process of a (patient, provider, donor) triple might need to be done in hours instead of the weeks or months it might take for manually finding a donor for a particular treatment. Patients are screened for financial inability to pay, providers are screened to avoid cases where they cannot provide the treatment or they get paid and do not provide the treatment, and donors are filtered based on donor criteria for what they will fund (and their bona fides as donors).

In one approach, as a patient record is created, the patient record is assigned a treatment code representing the treatment they are seeking. The provider database has provider records, each with one or more treatment code representing the treatments they can provide. The donor database has donor records, each with one or more treatment code representing the treatments they agree to fund. Using that information, the back-end server can quickly curate and filter to find a match.

In a method of identifying and collecting curated patients' information, the back-end server might distribute collected data to one or several pre-selected healthcare provider(s) that are cross-referenced to screen for the ability and willingness to provide treatment of patient condition(s), and selecting and matching from diverse financial donors (private, public and governmental) for reimbursement of medical services. This process might use multidimensional analysis and classification of data that is trackable with full transparency. It embodies networked matching systems that includes plurality of computers to collect, retrieve and match patients, medical care providers (hospitals) and financial donors to efficiently, accurately, cost-effectively, and expeditiously provide value-based care to underserved patients who have limited financial means.

In one process, a patient fills out a questionnaire, which includes some information including, but not limited to: medical history, gender, age, basic financial information for ability/inability to pay, geographical location, treatability by telemedicine, type of medical condition, severity of the condition, urgency for treatment, frequency for treatment, etc. A set of such information and data might get analyzed, classified and matched against care providers who have certain corresponding criteria with the patient. These criteria may include but are not limited to: geographical location, type of hospitals, focus areas/level of medical expertise, capacity for treatment, physicians/medical staff willingness & permission to treat in another hospital, access to telemedicine, etc.

With the multidimensional matching system, an Online Analytical Processing (OLAP) system might analyze, retrieve and subsequently respond effectively and efficiently to multidimensional queries. In addition, the matching method can go through a classification process via classifier algorithms. These classifiers hold features or values that have been assigned specific variables.

Once the selection process for patient and care provider is completed (as soon as and almost in parallel with), another multidimensional query will take place for the selection process of the donor(s). The already curated data that contains information about patient, medical care provider and the financial need for rendering such medical service will go through a more detailed classification process to find the right matching donor(s) from the pool of private, public, corporate, foundations and government agency donors. This matching process narrows down the financial donors in return for the treatment of the patient care.

In this manner, curated datasets can be used to match a patient to a provider and a donor. The financial analysis portion might consider the patient's ability to pay, resources available (such as liquid funds).

Variations

In particular embodiments, the provider servers and donor servers can operate and respond to messages from the back-end server without needing human interaction. In some embodiments, messages from the back-end server to a provider server are evaluated by someone working for the provider associated with the provider server. In some embodiments, messages from the back-end server to a donor server are evaluated by someone working for the donor associated with the donor server. The back-end server can perform matching patient-provider-donor automatically and can automatically send messages to the patient, to the provider, and to the donor, as needed.

This offers more efficiency and introduces steps beyond a matching/selecting process. Participation from participants (patient, provider, donor) can be automated after the initial step from the patient and the responses from selected/ matched providers and donors. The back-end server can store, analyze, select, match, and notify the stakeholders (e.g., patient, provider, donor) as needed. This offers more efficiency and introduces steps beyond regular commonly practiced matching/selecting processes.

Data from disparate sources for patients, providers, and donors can be harmonized and standardized, to provide accuracy, compatibility while avoiding redundancy and ease of integration. For example, a patient's information can be coded with unique identifiers, and provider's clinical data and donor's financial data can also be coded and marked with unique identifiers for faster and smarter matching. Various types of encryption and firewalls can be applied/ installed to protect privacy and support the integrity of data.

The back-end server might include data repositories for OLTP (Online Transaction Processing) for an operational system (database) and OLAP (Online Analytical Processing) for data warehousing. OLTP might be used to offer fast query processing while keeping data integrity in a multi-access platform. It also preserves compatibility with EHR (electronic Health Record) and EMR (electronic Medical Record) software that might be used by healthcare providers. OLAP offers multi-dimensional views and complex query manipulation as well as aggregation of data sourced from the OLTP databases.

CONCLUSION

The above-described systems can provide funding for healthcare expenses for the uninsured/underinsured population in need of healthcare. Such funding processes can reduce the cost of uncompensated care provided by healthcare providers, such as hospitals. Uncompensated care might comprise charity care, where a healthcare provider understands at the outset that there will not be compensation for providing the healthcare, as well as uncollectable billings, where a healthcare provider determines after providing the healthcare that the bill is partially or not fully collectable. Uncompensated care cost might constitute 5-6% of a hospital's expenditures.

The full burden of uncompensated care does not fall solely on doctors, clinics and hospitals. There are various funding programs that can alleviate this drain. In the U.S., a majority of the funding for uncompensated care has been provided by the U.S. federal or state governments, with Medicare and Medicaid covering about 60% of the uncompensated care cost, local and state resources that constitutes approximately 38%, and less than 1% through private funds.

Utilizing various aspects of the above-described system(s), not only can they provide or promote healthcare funding to the underserved and democratize healthcare, but they also can promote reductions in the cost of uncompensated care and provide a substantial cost saving to the government, state, hospitals and taxpayers.

Further embodiments can be envisioned to one of ordinary skill in the art after reading this disclosure. In other embodiments, combinations or sub-combinations of the above disclosed invention can be advantageously made. The example arrangements of components are shown for purposes of illustration and it should be understood that combinations, additions, re-arrangements, and the like are contemplated in alternative embodiments of the present invention. For example, the operations of the hospital and hospital computers might be done instead by health clinics. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

What is claimed is:

1. A method of coordinating funding of healthcare procedures using a computer, comprising:
    providing,
        a front-end web server to interface to one or more patient systems,
        a back-end server system coupled to the front-end web server to receive patient information, the back-end server including at least one of a patient dataset including patient details, a provider dataset including a procedure record, and a donor dataset including a donation criteria,
        a healthcare facility computer system that provides information about a procedure needed by a patient unable to pay for the procedure, providing the information to the back-end server system, and
        a donor computer system, for accepting and receiving messages from the back-end server system about funding patient procedures;
    receiving, at the front-end web server, a request for medical care, wherein the request for medical care is a first request initiated by a patient and recorded in the healthcare facility computer system;
    coding, through a business/application logic module in the back-end server system, at least one of the patient details, the procedure record, and the donation criteria with unique identifiers;
    filtering at least one of the patient details with the unique identifier into a patient curated database, the procedure record with the unique identifier into a curated provider database, and the donation criteria with the unique identifier into a curated donor database;
    obtaining, in the curated provider database, the procedure record that includes data about a procedure that corresponds to the first request for medical care;
    determining, using each of the patient curated database and the provider curated database, that the patient requires the procedure and that the patient is unable to pay costs of the procedure;
    sending an urgent notification message, from the business/application logic module of the back-end server system to a provider silo, to identify available healthcare providers;
    accessing the curated donor database to identify donor records corresponding to donors that have the donation criteria and that are donor records with the donation criteria that match the procedure referenced in the procedure record;
    filtering a plurality of requests including the first request to a filtered set of filtered requests wherein each filtered request relates a related procedure record and a related donor record;
    sending a request, through a donor query module in the curated donor database, to a donor;
    for each of the filtered requests, sending an urgent notification approval message with the patient details and procedure details to a donor computer system of a selected donor, wherein the urgent notification approval message indicates a consistency between a filtered request and donor donation criteria;
    receiving approval from the donor computer system for the selected donor to fund the procedure;
    effecting funds transfer from the selected donor to a healthcare facility operator for the procedure; and
    performing the procedure on the patient.

2. The method of claim 1, wherein the urgent notification approval message includes the patient details for the selected donor to determine that funding is appropriate and omits patient personally identifying information.

3. The method of claim 1, further comprising matching the plurality of requests and a plurality of donors, using a healthcare facility computer system, that processes the plurality of requests and a plurality of donor records to derive a matched set of donor requests wherein the matched set of donor requests identifies a number of procedures that can be funded.

4. The method of claim 1, wherein the computer system further includes a matching module, that processes the plurality of requests and a plurality of donor records to derive a matched set of donor requests, wherein the matched set of donor requests determines a number of procedures that can be funded.

5. The method of claim 1, wherein the filtering is performed by the back-end server system.

6. The method of claim 1, wherein the back-end server system includes data repositories for online transaction processing for an operational system and for online analytical processing system for data warehousing.

7. The method of claim 6, wherein the online analytical processing system is configured to perform a step of matching the plurality of requests and a plurality of donors.

8. The method of claim 1, further comprising a telemedicine module in the healthcare facility computer system configured to permit communication between the patient and the healthcare facility.

* * * * *